US012583814B2

(12) United States Patent
Kim et al.

(10) Patent No.: US 12,583,814 B2
(45) Date of Patent: Mar. 24, 2026

(54) COMPOUND AND ORGANIC LIGHT EMITTING DEVICE COMPRISING THE SAME

(71) Applicant: LG CHEM, LTD., Seoul (KR)

(72) Inventors: Minjun Kim, Daejeon (KR); Dong Hoon Lee, Daejeon (KR); Sang Duk Suh, Daejeon (KR); Min Woo Jung, Daejeon (KR); Seulchan Park, Daejeon (KR); Sunghyun Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 412 days.

(21) Appl. No.: 18/035,106

(22) PCT Filed: Feb. 16, 2022

(86) PCT No.: PCT/KR2022/002287
§ 371 (c)(1),
(2) Date: May 2, 2023

(87) PCT Pub. No.: WO2022/177288
PCT Pub. Date: Aug. 25, 2022

(65) Prior Publication Data
US 2024/0025840 A1 Jan. 25, 2024

(30) Foreign Application Priority Data

Feb. 16, 2021 (KR) ......................... 10-2021-0020508
Feb. 16, 2022 (KR) ......................... 10-2022-0020090

(51) Int. Cl.
| | |
|---|---|
| C07C 211/54 | (2006.01) |
| C07C 211/61 | (2006.01) |
| C07D 209/58 | (2006.01) |
| C07D 307/91 | (2006.01) |
| C07D 333/76 | (2006.01) |
| C07D 407/12 | (2006.01) |
| C07D 409/12 | (2006.01) |
| C07D 411/12 | (2006.01) |
| C09K 11/06 | (2006.01) |
| H10K 85/60 | (2023.01) |
| H10K 50/18 | (2023.01) |

(52) U.S. Cl.
CPC .......... *C07C 211/54* (2013.01); *C07C 211/61* (2013.01); *C07D 209/58* (2013.01); *C07D 307/91* (2013.01); *C07D 333/76* (2013.01); *C07D 407/12* (2013.01); *C07D 409/12* (2013.01); *C07D 411/12* (2013.01); *C09K 11/06* (2013.01); *H10K 85/622* (2023.02); *H10K 85/631* (2023.02); *H10K 85/6572* (2023.02); *H10K 85/6574* (2023.02); *H10K 85/6576* (2023.02); *H10K 50/181* (2023.02)

(58) Field of Classification Search
CPC .................................................... C07C 211/54
See application file for complete search history.

(56) References Cited

U.S. PATENT DOCUMENTS

| | | | |
|---|---|---|---|
| 6,696,178 | B2 | 2/2004 | Igarashi |
| 8,968,883 | B2 | 3/2015 | Rostovtsev et al. |
| 2004/0251816 | A1 | 12/2004 | Leo et al. |
| 2006/0052641 | A1 | 3/2006 | Funahashi |
| 2007/0155991 | A1 | 7/2007 | Funahashi |
| 2009/0195149 | A1 | 8/2009 | Funahashi |
| 2011/0037056 | A1 | 2/2011 | Dubois et al. |
| 2011/0227053 | A1 | 9/2011 | Bae et al. |
| 2011/0288292 | A1 | 11/2011 | Parham et al. |
| 2013/0126852 | A1 | 5/2013 | Gao et al. |
| 2013/0187140 | A1 | 7/2013 | Rostovtsev et al. |
| 2015/0069347 | A1 | 3/2015 | Kim et al. |
| 2017/0352815 | A1 | 12/2017 | Howard et al. |
| 2018/0208834 | A1 | 7/2018 | Goto et al. |
| 2019/0013490 | A1 | 1/2019 | Cho et al. |
| 2019/0214573 | A1 | 7/2019 | Ryu et al. |
| 2020/0058877 | A1 | 2/2020 | Cha et al. |
| 2022/0131083 | A1 | 4/2022 | Lee et al. |

(Continued)

FOREIGN PATENT DOCUMENTS

| | | |
|---|---|---|
| CN | 1711334 A | 12/2005 |
| CN | 107778212 A | 3/2018 |
| CN | 107778213 A | 3/2018 |

(Continued)

*Primary Examiner* — Golam M Shameem

(74) *Attorney, Agent, or Firm* — Bryan Cave Leighton Paisner LLP

(57) ABSTRACT

A compound represented by Chemical Formula 1 and an organic light emitting device are provided. The compound is used as a material for an organic material layer of the organic light emitting device and provides improved efficiency, low driving voltage and enhanced lifetime.

[Chemical Formula 1]

11 Claims, 1 Drawing Sheet

(56) References Cited

U.S. PATENT DOCUMENTS

| | | | |
|---|---|---|---|
| 2022/0336757 A1 | 10/2022 | Jung et al. | |
| 2023/0371365 A1 | 11/2023 | Ma et al. | |

FOREIGN PATENT DOCUMENTS

| | | |
|---|---|---|
| CN | 108218664 A | 6/2018 |
| CN | 108586188 A | 9/2018 |
| CN | 110003090 A | 7/2019 |
| CN | 110498765 A | 11/2019 |
| CN | 113636943 A | 11/2021 |
| CN | 114479835 A | 5/2022 |
| CN | 115244727 A | 10/2022 |
| CN | 116508410 A | 7/2023 |
| JP | 3035622 B2 | 2/2000 |
| JP | 2006-151844 A | 6/2006 |
| JP | 4205059 B2 | 1/2009 |
| JP | 2009-027092 A | 2/2009 |
| JP | 2009-161470 A | 7/2009 |
| JP | 4677221 B2 | 4/2011 |
| JP | 2012512275 A | 5/2012 |
| JP | 2013501783 A | 1/2013 |
| JP | 2013538453 A | 10/2013 |
| JP | 2019520347 A | 7/2019 |
| JP | 2019524741 A | 9/2019 |
| KR | 10-2000-0051826 A | 8/2000 |
| KR | 10-2005-0086518 A | 8/2005 |
| KR | 10-2010-0056398 A | 5/2010 |
| KR | 10-1031719 B1 | 4/2011 |
| KR | 10-2015-0028935 A | 3/2015 |
| KR | 10-2016-0006633 A | 1/2016 |
| KR | 10-2017-0023388 A | 3/2017 |
| KR | 10-1885898 B1 | 8/2018 |
| KR | 10-2020-0072211 A | 6/2020 |
| KR | 10-2191991 B1 | 12/2020 |
| KR | 10-2021-0144603 A | 11/2021 |
| KR | 10- 2022-0055411 A | 5/2022 |
| TW | 201036938 A | 10/2010 |
| WO | 2003-012890 A2 | 2/2003 |
| WO | 2004-044088 A1 | 5/2004 |
| WO | 2008-149968 A1 | 12/2008 |
| WO | 2009-008351 A1 | 1/2009 |
| WO | 2010-058946 A1 | 8/2010 |
| WO | 2020-122460 A1 | 6/2020 |
| WO | 2020-185054 A1 | 11/2020 |
| WO | 2021-235906 A1 | 11/2021 |

[FIG. 1]

| |
|---|
| 5 |
| 4 |
| 3 |
| 2 |
| 1 |

[FIG. 2]

| |
|---|
| 5 |
| 9 |
| 8 |
| 4 |
| 3 |
| 7 |
| 6 |
| 2 |
| 1 |

COMPOUND AND ORGANIC LIGHT EMITTING DEVICE COMPRISING THE SAME

CROSS-REFERENCE TO RELATED APPLICATION(S)

This application is a National Phase entry pursuant to 35 U.S.C. § 371 of International Application No. PCT/KR2022/002287 filed on Feb. 16, 2022, and claims priority to and the benefit of Korean Patent Application No. 10-2021-0020508 filed on Feb. 16, 2021 and Korean Patent Application No. 10-2022-0020090 filed on Feb. 16, 2022, the disclosures of which are incorporated herein by reference in their entirety.

FIELD OF DISCLOSURE

The present disclosure relates to a novel compound and an organic light emitting device comprising the same.

BACKGROUND

In general, an organic light-emitting phenomenon refers to a phenomenon where electric energy is converted into light energy by using an organic material. The organic light emitting device using the organic light-emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a need for continuous development of new materials for the organic materials used in the organic light emitting devices as described above.

RELATED ART

Korean Unexamined Patent Publication No. 10-2000-0051826

SUMMARY

It is an object of the present disclosure to provide a novel organic light-emitting material and an organic light emitting device comprising the same.

According to an aspect of the present disclosure, there is provided a compound represented by the following Chemical Formula 1:

[Chemical Formula 1]

in Chemical Formula 1, one of $R_1$ to $R_{12}$ is a substituent represented by the following Chemical Formula 2, and the rest $R_1$ to $R_{12}$ are each independently hydrogen or deuterium,

[Chemical Formula 2]

in Chemical Formula 2, $L_1$ is a substituted or unsubstituted phenylene, a substituted or unsubstituted biphenyldiyl, a substituted or unsubstituted naphthalenediyl, or $L_2$ and $L_3$ are each independently a single bond; a substituted or unsubstituted $C_{6-60}$ arylene, or a substituted or unsubstituted $C_{2-60}$ heteroarylene containing one or more selected from the group consisting of N, O and S, $Ar_1$ is a substituted or unsubstituted $C_{6-60}$ aryl; or a substituted or unsubstituted $C_{2-60}$ heteroaryl containing one or more selected from the group consisting of N, O and S, and $Ar_2$ is biphenylyl, terphenylyl, naphthyl, phenanthrenyl, phenyl naphthyl, dibenzofuranyl, dibenzothiophenyl, phenyl carbazolyl, dimethyl fluorenyl, benzonaphthofuranyl, or benzonaphthothiophenyl.

According to another aspect of the present disclosure, there is provided an organic light emitting device comprising: a first electrode; a second electrode disposed to face the first electrode; and an organic material layer including one or more layers between the first electrode and the second electrode, wherein one or more layers of the organic material layer include the compound represented by Chemical Formula 1.

The above-mentioned compound represented by Chemical Formula 1 can be used as a material for an organic material layer of an organic light emitting device, and can improve the efficiency, achieve low driving voltage and/or improve lifetime characteristics in the organic light emitting device. Particularly, the compound represented by Chemical Formula 1 described above can be used as a light-emitting material.

BRIEF DESCRIPTION OF THE DRAWINGS

FIG. 1 shows an example of an organic light emitting device comprising a substrate 1, an anode 2, an electron blocking layer 3, a light emitting layer 4 and a cathode 5.

FIG. 2 shows an example of an organic light emitting device comprising a substrate 1, an anode 2, a hole injection layer 6, a hole transport layer 7, an electron blocking layer 3, a light emitting layer 4, a hole blocking layer 8, an electron transport and injection layer 9 and a cathode 5.

DETAILED DESCRIPTION

Hereinafter, embodiments of the present disclosure will be described in more detail to facilitate understanding of the invention.

Provided herein is the compound represented Chemical Formula 1.

As used herein, the notation $\overset{\xi}{\rightleftharpoons}$ or $\vdots$ means a bond linked to another substituent group.

As used herein, the term "substituted or unsubstituted" means being unsubstituted or substituted with one or more substituents selected from the substituent group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heteroaryl group containing one or more of N, O and S atoms, or being unsubstituted or substituted with a substituent from the above substituent group which is further substituted by one or more selected from the above substituent group.

In the present disclosure, the carbon number of a carbonyl group is not particularly limited, but is preferably 1 to 40. Specifically, the carbonyl group may be a substituent group having the following structural formulas, but is not limited thereto.

In the present disclosure, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a substituent group having the following structural formulas, but is not limited thereto.

In the present disclosure, the carbon number of an imide group is not particularly limited, but is preferably 1 to 25. Specifically, the imide group may be a substituent group having the following structural formulas, but is not limited thereto.

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group may be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methyl-hexyl, and the like, but are not limited thereto.

In the present disclosure, the alkenyl group may be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it may be a monocyclic aryl group or a polycyclic aryl group. According to one embodiment, the carbon number of the aryl group is 6 to 30. According to one embodiment, the carbon number of the aryl group is 6 to 20. The aryl group may be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, a fluorenyl group, or the like, but is not limited thereto.

In the present disclosure, the fluorenyl group may be substituted, and two substituents may be connected to each other to form a spiro structure. In the case where the fluorenyl group is substituted, and the like can be formed. However, the structure is not limited thereto.

In the present disclosure, a heteroaryl group is a heteroaryl group containing one or more of O, N, Si and S as a heteroatom, and the carbon number thereof is not particularly limited, but is preferably 2 to 60. According to an exemplary embodiment of heteroaryl, the heteroaryl group has 6 to 30 carbon atoms. According to an exemplary embodiment, the heteroaryl group has 6 to 20 carbon atoms. Examples of heteroaryl groups include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group and the arylamine group is the same as the above-mentioned examples of the aryl group. In the present disclosure, the alkyl group in the aralkyl group, the alkylaryl group and the alkylamine group is the same as the above-mentioned examples of the alkyl group. In the present disclosure, the heteroaryl in the heteroarylamine may be applied to the above-mentioned description of the heteroaryl group. In the present disclosure, the alkenyl group in the aralkenyl group is the same as the above-mentioned examples of the alkenyl group. In the present disclosure, the above-mentioned description of the aryl group may be applied except that the arylene is a divalent group. In the present disclosure, the above-mentioned description of the heteroaryl group may be applied except that the heteroarylene is a divalent group. In the present disclosure, the above-mentioned description of the aryl group or cycloalkyl group may be applied except that the hydrocarbon ring is not a monovalent group but formed by combining two substituent groups. In the present disclosure, the above-mentioned description of the heteroaryl group may be applied, except that the heteroaryl is not a monovalent group but formed by combining two substituent groups.

Preferably, one of $R_1$ to $R_3$, $R_5$ to $R_9$, $R_{11}$ and $R_{12}$ is a substituent represented by Chemical Formula 2, the rest of $R_1$ to $R_3$, $R_5$ to $R_9$, $R_{11}$ and $R_{12}$ are each independently hydrogen or deuterium, and $R_4$ and $R_{10}$ may be each independently hydrogen or deuterium. More preferably, one of $R_1$ to $R_3$, $R_5$ to $R_9$, $R_{11}$ and $R_{12}$ may be a substituent represented by Chemical Formula 2, the rest of $R_1$ to $R_3$, $R_5$ to $R_9$, $R_{11}$ and $R_{12}$ are each independently hydrogen, and $R_4$ and $R_{10}$ may be each independently hydrogen.

Preferably, $L_1$ may be phenylene unsubstituted or substituted with one phenyl, biphenyldiyl unsubstituted or substituted with one phenyl, or naphthalendiyl unsubstituted or substituted with one phenyl, or More preferably, $L_1$ may be one selected from the following:

-continued

-continued

More preferably, L$_1$ may be phenylene unsubstituted or substituted with one phenyl, biphenyldiyl unsubstituted or substituted with one phenyl, or naphthalendiyl.

More preferably, L$_1$ may be one selected from the following:

-continued

More preferably, $R_5$ or $R_{11}$ is a substituent represented by Chemical Formula 2, and $L_1$ may be one selected from the following:

Preferably, $L_2$ and $L_3$ may be each independently a single bond, a substituted or unsubstituted $C_{6-20}$ arylene, or a substituted or unsubstituted $C_{2-20}$ heteroarylene containing at least one selected from the group consisting of N, O and S.

More preferably, $L_2$ and $L_3$ may be each independently a single bond, phenylene, phenylene substituted with one phenyl, biphenyldiyl, biphenyldiyl substituted with one phenyl, or naphthalenediyl.

Most preferably, $L_2$ and $L_3$ may be each independently a single bond or one selected from the following:

-continued

Preferably, $Ar_1$ may be a substituted or unsubstituted $C_{6-20}$ aryl; or a substituted or unsubstituted $C_{2-20}$ heteroaryl containing one or more selected from the group consisting of N, O and S.

More preferably, $Ar_1$ may be phenyl, biphenylyl, terphenylyl, naphthyl, phenanthrenyl, phenyl naphthyl, dibenzofuranyl, dibenzothiophenyl, phenyl carbazole, dimethyl fluorenyl, benzonaphthofuranyl, or benzonaphthothiophenyl.

More preferably, $Ar_1$ may be one selected from the following:

-continued

-continued

15

-continued

16

-continued

More preferably, Ar$_1$ may be one selected from the following:

17

-continued

18

-continued

Preferably, Ar$_2$ may be one selected from the following:

19

20

21

-continued

22

-continued

Representative examples of the compound represented by Chemical Formula 1 are as follows:

23

24

25

26

27

28

29

30

31

32

33

34

35
-continued

36
-continued

37

38

39

40

41

42

43

44

45

46

47

48

49
-continued

50
-continued

51

52

53

54

55

56

59

60

61

62

63

64

65

66

67

68

69

70

71

72

73

-continued

74

-continued

75

76

77
-continued

78
-continued

79

80

81

82

83
-continued

84
-continued

85

86

87

-continued

88

-continued

89

90

91                                                          92

93

94

95
-continued

96
-continued

97
-continued

98
-continued

99
-continued

100
-continued

101

102

103

104

-continued

-continued

107

108

109

110

111

112

113
-continued

114
-continued

115

116

117

118

119

-continued

120

-continued

121

-continued

122

-continued

123

124

125
-continued

126
-continued

127

-continued

128

-continued

129

130

131

132

133
-continued

134
-continued

135

136

137
-continued

138
-continued

139

140

-continued

-continued

143

144

147

148

151

152

-continued

-continued

155

-continued

156

-continued

157

158

159

160

161

162

163

164

165

166

167

168

169

170

171

-continued

172

-continued

173

174

175

176

177

178

179

180

181

182

183

184

185

186

187

188

189

190

191

192

193

194

195

196

197

198

199

200

201

202

203

204

205
-continued

206
-continued

207
-continued

208
-continued

209

210

211

212

213
-continued

214
-continued

215

216

217

218

219

220

221

222

223

224

-continued

227

228

-continued

229

230

231

232

233 234

-continued

237

238

-continued

239

240

241

242

243

244

245

246

247

248

249

250

251

252

253

254

255

256

257

258

259

260

-continued

261

262

263

264

265

266

-continued

267

268

269

270

271

272

273

274

275

276

-continued

-continued

281

282

283

284

285

286

-continued 289
290

291

292

293

294

295

296

-continued

-continued

299

300

301

302

303

304

305

306

307

308

-continued

311

312

313

314

315

316

317

318

319

320

321

322

-continued

325

326

327

328

-continued

331

332

333

334

-continued

335

336

337

338

-continued

341

342

-continued

345

346

347

348

349

350

351

352

353

354

355

356

357

358

-continued

-continued

-continued

363

364

365

366

-continued

371

372

373

374

375

376

-continued

-continued

381

382

383

384

-continued

385

386

-continued

387

388

-continued

-continued

391                                              392

393

394

395

396

397

398

399

400

-continued

401

402

-continued

The compounds represented by Chemical Formula 1, of which one of $R_1$ to $R_{12}$ is a substituent represented by the following Chemical Formula 2 and the rest of $R_1$ to $R_{12}$ are hydrogen, can be prepared by a preparation method as shown in the following Reaction Scheme 1 as an example, and other remaining compounds can be prepared in a similar manner.

[Reaction Scheme 1]

-continued in Reaction Scheme 1, $L_1$ to $L_3$, $Ar_1$ and $Ar_2$ are the same as defined in Chemical Formula 1, and X is halogen, preferably chloro or bromo.

Reaction Scheme 1 is a Suzuki coupling reaction, which is preferably carried out in the presence of a palladium catalyst and a base, and a reactive group for the Suzuki coupling reaction can be modified as known in the art. The above preparation method may be further embodied in Preparation Examples described hereinafter.

In another embodiment of the present disclosure, there is provided an organic light emitting device including the compound represented by Chemical Formula 1. In one example, the present disclosure provides an organic light emitting device comprising: a first electrode; a second electrode disposed to face the first electrode; and an organic material layer including one or more layers between the first electrode and the second electrode, wherein one or more layers of the organic material layer include the compound represented by Chemical Formula 1.

The organic material layer of the organic light emitting device of the present disclosure may have a single-layer structure, or it may have a multilayered structure in which two or more layers are stacked. For example, the organic light emitting device of the present disclosure may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of layers in the organic material layer.

Further, the organic material layer may include a light emitting layer, wherein the light emitting layer may include the compound represented by Chemical Formula 1.

Further, the organic material layer may include a hole transport layer, a hole injection layer, or a layer for simultaneously performing hole transport and injection, wherein the hole transport layer, the hole injection layer, or the layer for simultaneously performing hole transport and injection may include the compound represented by Chemical Formula 1.

Further, the organic material layer may include an electron injection layer, an electron transport layer, or an electron injection and transport layer, wherein the electron injection layer, the electron transport layer, or the electron injection and transport layer may include the compound represented by Chemical Formula 1.

Further, the organic light emitting device according to the present disclosure may be a normal type organic light emitting device in which an anode, an organic material layer including one or more layers and a cathode are sequentially stacked on a substrate. Further, the organic light emitting device according to the present disclosure may be an inverted type organic light emitting device in which a cathode, an organic material layer including one or more layers and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, an electron blocking layer 3, a light emitting layer 4 and a cathode 5. FIG. 2 shows an example of an organic light emitting device comprising a substrate 1, an anode 2, a hole injection layer 6, a hole transport layer 7, an electron blocking layer 3, a light emitting layer 4, a hole blocking layer 8, an electron transport and injection layer 9 and a cathode 5. In such a structure, the compound represented by Chemical Formula 1 may be included in the hole transport layer, the electron blocking layer or the light emitting layer.

The organic light emitting device according to the present disclosure may be manufactured by materials and methods known in the art, except that at least one layer of the organic material layer includes the compound represented by Chemical Formula 1. Further, when the organic light emitting device includes a plurality of layers in the organic material layer, the plurality of layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming an organic material layer including the hole injection layer, the hole transport layer, the light emitting layer and the electron transport layer thereon, and then depositing a material that can be used as the cathode thereon. In addition to such a method, the organic light emitting device can be manufactured by sequentially depositing a cathode material, an organic material layer and an anode material on a substrate.

Further, the compound represented by Chemical Formula 1 can be formed into an organic material layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive compounds such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and further is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport layer is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto. Preferably, the compound represented by Chemical Formula 1 can be used as a material for the hole transport layer.

The electron blocking layer is a layer provided between the hole transport layer and the light emitting layer in order to prevent the electrons injected in the cathode from being transferred to the hole transport layer without being recombined in the light emitting layer, which may also be referred to as an electron inhibition layer. The electron blocking layer is preferably a material having the smaller electron affinity than the electron transport layer. Preferably, the compound represented by Chemical Formula 1 can be used as a material for the electron blocking layer.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene)(PPV)-based polymer; a spiro compound; polyfluorene, rubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocycle-containing compounds include carbazole derivatives, dibenzofuran derivatives, ladder-type furan compounds, pyrimidine derivatives, and the like, but are not limited thereto. Preferably, the compound represented by Chemical Formula 1 may be included as a host material.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

Preferably, the dopant material may be at least one selected from the following:

409

410

411

-continued

412

-continued

413
-continued

414
-continued

The hole blocking layer is a layer provided between the electron transport layer and the light emitting layer in order to prevent the holes injected in the anode from being transferred to the electron transport layer without being recombined in the light emitting layer, which may also be referred to as a hole inhibition layer. The hole blocking layer is preferably a material having the large ionization energy.

The electron transport layer is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracar-boxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hy-droxyquinolinato lithium, bis(8-hydroxyquinolinato)zinc, bis(8-hydroxyquinolinato)copper, bis(8-hydroxyquinoli-nato)manganese, tris(8-hydroxyquinolinato)aluminum, tris (2-methyl-8-hydroxyquinolinato)aluminum, tris(8-hydroxy-quinolinato)gallium, bis(10-hydroxybenzo[h]quinolinato) beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

On the other hand, in the present disclosure, the "electron injection and transport layer" is a layer that performs both the roles of the electron injection layer and the electron transport layer, and the materials that perform the roles of each layer may be used alone or in combination, without being limited thereto.

The organic light emitting device according to the present disclosure may be a bottom emission device, a top emission device, or a double-sided light emitting device, and particu-larly, may be a bottom emission device that requires rela-tively high luminous efficiency.

In addition, the compound represented by Chemical For-mula 1 may be included in an organic solar cell or an organic transistor in addition to the organic light emitting device.

The compound represented by Chemical Formula 1 and the preparation of an organic light emitting device including the same will be described in detail by way of Examples. However, the following examples are for illustrative pur-poses only, and the scope of the present disclosure is not limited thereto.

PREPARATION EXAMPLES

Preparation Example 1

-continued amine1

1

Compound A (15 g, 57.1 mmol) and Compound amine1 (34 g, 59.9 mmol) were added to 300 ml of THF under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 12 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 29.1 g of Compound 1. (Yield: 68%, MS: $[M+H]^+=750$)

Preparation Example 2

A

417

-continued

418

Preparation Example 3 amine2

2 amine3

3

Compound A (15 g, 57.1 mmol) and Compound amine2 (32.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 11 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 31 g of Compound 2. (Yield: 75%, MS: $[M+H]^+=724$)

Compound A (15 g, 57.1 mmol) and Compound amine3 (24.9 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 25.2 g of Compound 3. (Yield: 74%, MS: $[M+H]^+=598$)

419

Preparation Example 4

A

B(OH)₂ amine4

$\xrightarrow[\text{THF/H}_2\text{O}]{\text{Pd(t-Bu}_3\text{P})_2,\ \text{K}_2\text{CO}_3}$

4

420 pressure. The concentrated compound was purified by silica gel column chromatography to prepare 26.8 g of Compound 4. (Yield: 65%, MS: $[M+H]^+=724$)

Preparation Example 5

A

B(OH)₂ amine5

$\xrightarrow[\text{THF/H}_2\text{O}]{\text{Pd(t-Bu}_3\text{P})_2,\ \text{K}_2\text{CO}_3}$

5

Compound A (15 g, 57.1 mmol) and Compound amine4 (32.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced Compound A (15 g, 57.1 mmol) and Compound amine5 (31.9 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 12 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 26.5 g of Compound 5. (Yield: 65%, MS: [M+H]$^+$=714)

Preparation Example 6 amine6

6

Compound A (15 g, 57.1 mmol) and Compound amine6 (28.3 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 27.2 g of Compound 6. (Yield: 73%, MS: [M+H]$^+$=654)

Preparation Example 7 amine7

7

Compound A (15 g, 57.1 mmol) and Compound amine7 (27.2 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 28.3 g of Compound 7. (Yield: 78%, MS: [M+H]$^+$=637)

Preparation Example 8

A amine8

Pd(t-Bu₃P)₂, K₂CO₃
THF/H₂O

8

Compound A (15 g, 57.1 mmol) and Compound amine8 (24.3 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 21.1 g of Compound 8. (Yield: 63%, MS: [M+H]⁺=588)

Preparation Example 9

A amine9

Pd(t-Bu₃P)₂, K₂CO₃
THF/H₂O

9

Compound A (15 g, 57.1 mmol) and Compound amine9 (29.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added.

After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 24.2 g of Compound 9. (Yield: 63%, MS: [M+H]$^+$=674)

Preparation Example 10 amine10

10

Compound A (15 g, 57.1 mmol) and Compound amine10 (29.5 g, 59.9 mmol) were added to 300 ml of THF under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 11 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 27.3 g of Compound 10. (Yield: 71%, MS: [M+H]$^+$=674)

Preparation Example 11 amine11

11

Compound A (15 g, 57.1 mmol) and Compound amine11 (29.5 g, 59.9 mmol) were added to 300 ml of THF under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 26.5 g of Compound 11. (Yield: 69%, MS: $[M+H]^+=674$)

Preparation Example 12

Compound A (15 g, 57.1 mmol) and Compound amine12 (32.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 12 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 24.8 g of Compound 12. (Yield: 60%, MS: $[M+H]^+=724$)

Preparation Example 13

-continued

13

-continued amine14

$$\xrightarrow[\text{THF/H}_2\text{O}]{\substack{\text{Pd(t-Bu}_3\text{P)}_2, \\ \text{K}_2\text{CO}_3}}$$

Compound A (15 g, 57.1 mmol) and Compound amine13 (34 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 33.8 g of Compound 13. (Yield: 79%, MS: [M+H]$^+$=750)

Preparation Example 14

+

A

14

Compound A (15 g, 57.1 mmol) and Compound amine14 (31 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 30.3 g of Compound 14. (Yield: 76%, MS: [M+H]$^+$=700)

Preparation Example 15

Preparation Example 16 amine15 amine16

15

16

Compound B (15 g, 57.1 mmol) and Compound amine15 (24.9 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 21.8 g of Compound 15. (Yield: 64%, MS: [M+H]$^+$=598)

Compound B (15 g, 57.1 mmol) and Compound amine16 (31 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 26.3 g of Compound 16. (Yield: 66%, MS: [M+H]$^+$=700)

433

Preparation Example 17

434

Preparation Example 18

10 amine17

25 amine18

17

18

Compound B (15 g, 57.1 mmol) and Compound amine17 (29.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 12 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 27.7 g of Compound 17. (Yield: 72%, MS: [M+H]$^+$=674)

Compound B (15 g, 57.1 mmol) and Compound amine18 (27.9 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 12 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 24.4 g of Compound 18. (Yield: 66%, MS: [M+H]$^+$=648)

| 435 | 436 |
|---|---|
| Preparation Example 19 | Preparation Example 20 | amine19

19 amine20

20

Compound B (15 g, 57.1 mmol) and Compound amine19 (28.1 g, 59.9 mmol) were added to 300 ml of THF under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 27.5 g of Compound 19. (Yield: 74%, MS: [M+H]$^+$=652)

Compound B (15 g, 57.1 mmol) and Compound amine20 (30.3 g, 59.9 mmol) were added to 300 ml of THF under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 28.3 g of Compound 20. (Yield: 72%, MS: [M+H]$^+$=688)

437

Preparation Example 21

438

Preparation Example 22 amine21

21 amine22

22

Compound B (15 g, 57.1 mmol) and Compound amine21 (28.9 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 11 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 25.8 g of Compound 21. (Yield: 68%, MS: [M+H]$^+$=664)

Compound B (15 g, 57.1 mmol) and Compound amine22 (30.3 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 30.6 g of Compound 22. (Yield: 78%, MS: [M+H]$^+$=688)

Preparation Example 23

C amine23

Pd(t-Bu₃P)₂,
K₂CO₃
THF/H₂O

23

Compound C (15 g, 57.1 mmol) and Compound amine23 (26.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 24.6 g of Compound 23. (Yield: 69%, MS: [M+H]⁺=624)

Preparation Example 24

C amine24

Pd(t-Bu₃P)₂,
K₂CO₃
THF/H₂O

24

Compound C (15 g, 57.1 mmol) and Compound amine24 (27.9 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 11 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 27.3 g of Compound 24. (Yield: 74%, MS: $[M+H]^+$=648)

Preparation Example 25 amine25

25

Compound C (15 g, 57.1 mmol) and Compound amine25 (26.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 11 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 23.5 g of Compound 25. (Yield: 66%, MS: $[M+H]^+$=624)

Preparation Example 26

C amine26

26

Compound C (15 g, 57.1 mmol) and Compound amine26 (30.1 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 24.2 g of Compound 26. (Yield: 62%, MS: $[M+H]^+$=684)

443 444

Preparation Example 27    Preparation Example 28

C amine27

27

D amine28

28

Compound C (15 g, 57.1 mmol) and Compound amine27 (26.7 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 11 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 24.7 g of Compound 27. (Yield: 69%, MS: [M+H]$^+$=628)

Compound D (15 g, 57.1 mmol) and Compound amine28 (26.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 12 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 24.2 g of Compound 28. (Yield: 68%, MS: [M+H]$^+$=624)

Preparation Example 29

D amine29

29

Compound D (15 g, 57.1 mmol) and Compound amine29 (32.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 12 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 24.8 g of Compound 29. (Yield: 60%, MS: $[M+H]^+=724$)

Preparation Example 30

D amine30

30

Compound D (15 g, 57.1 mmol) and Compound amine30 (31 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 31.9 g of Compound 30. (Yield: 80%, MS: $[M+H]^+=700$)

Preparation Example 31

D

447
-continued amine31

31

Compound D (15 g, 57.1 mmol) and Compound amine31 (29.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 30.8 g of Compound 31. (Yield: 80%, MS: [M+H]$^+$=674)

Preparation Example 32

D

+ amine32

448
-continued

32

Compound D (15 g, 57.1 mmol) and Compound amine32 (29.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 11 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 28.1 g of Compound 32. (Yield: 73%, MS: [M+H]$^+$=674)

Preparation Example 33

D

+ amine33

449

-continued

33

450

-continued

34

Compound D (15 g, 57.1 mmol) and Compound amine33 (28.9 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 29.9 g of Compound 33. (Yield: 79%, MS: [M+H]$^+$=664)

Compound D (15 g, 57.1 mmol) and Compound amine34 (29.1 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 27.4 g of Compound 34. (Yield: 72%, MS: [M+H]$^+$=668)

Preparation Example 34

Preparation Example 35

D

+

D

+ amine34 amine35

451

-continued

35

Compound D (15 g, 57.1 mmol) and Compound amine35 (30.3 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 23.5 g of Compound 35. (Yield: 60%, MS: [M+H]$^+$=688)

Preparation Example 36

D

+ amine36

$\xrightarrow{\text{Pd(t-Bu}_3\text{P)}_2,\ \text{K}_2\text{CO}_3}{\text{THF/H}_2\text{O}}$

452

-continued

36

Compound D (15 g, 57.1 mmol) and Compound amine36 (26.7 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 25.4 g of Compound 36. (Yield: 71%, MS: [M+H]$^+$=628)

Preparation Example 37

D

+ amine37

$\xrightarrow{\text{Pd(t-Bu}_3\text{P)}_2,\ \text{K}_2\text{CO}_3}{\text{THF/H}_2\text{O}}$ -continued

37

Compound D (15 g, 57.1 mmol) and Compound amine37 (31 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 31.9 g of Compound 37. (Yield: 80%, MS: $[M+H]^+=700$)

Preparation Example 38

D amine38

-continued

38

Compound D (15 g, 57.1 mmol) and Compound amine38 (24.9 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 23.5 g of Compound 38. (Yield: 69%, MS: $[M+H]^+=598$)

Preparation Example 39

D

455

-continued amine39

$$Pd(t\text{-}Bu_3P)_2,$$
$$K_2CO_3$$
$$\overline{THF/H_2O}$$

39

456

Preparation Example 40

D $$+$$

amine40

$$Pd(t\text{-}Bu_3P)_2,$$
$$K_2CO_3$$
$$\overline{THF/H_2O}$$

40

Compound D (15 g, 57.1 mmol) and Compound amine39 (32.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 11 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 30.6 g of Compound 39. (Yield: 74%, MS: [M+H]$^+$=724)

Compound D (15 g, 57.1 mmol) and Compound amine40 (34 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 30.8 g of Compound 40. (Yield: 72%, MS: [M+H]$^+$=750)

457 458

Preparation Example 41                    Preparation Example 42

D amine41

41

E amine42

42

Compound D (15 g, 57.1 mmol) and Compound amine41 (32.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 26 g of Compound 41. (Yield: 63%, MS: [M+H]$^+$=724)

Compound E (15 g, 57.1 mmol) and Compound amine42 (26.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 25.6 g of Compound 42. (Yield: 72%, MS: [M+H]$^+$=624)

<table>
<tr><td>459</td><td>460</td></tr>
<tr><td>Preparation Example 43</td><td>Preparation Example 44</td></tr>
</table>

E amine43

43

+

E amine44

44

Compound E (15 g, 57.1 mmol) and Compound amine43 (29.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 11 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 29.2 g of Compound 43. (Yield: 76%, MS: $[M+H]^+=674$)

Compound E (15 g, 57.1 mmol) and Compound amine44 (32.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 26.4 g of Compound 44. (Yield: 64%, MS: [M+H]$^+$=724)

Preparation Example 45 amine45

45 and then filtered, and the filtrate was distilled under reduced pressure. The concentrated compound was purified by silica gel column chromatography to prepare 22.4 g of Compound 45. (Yield: 70%, MS: [M+H]$^+$=562)

Preparation Example 46 amine46

46

Compound E (15 g, 57.1 mmol) and Compound amine45 (22.7 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, Compound E (15 g, 57.1 mmol) and Compound amine46 (31.8 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 25.6 g of Compound 46. (Yield: 63%, MS: $[M+H]^+=713$)

Preparation Example 47 amine47

47

Compound E (15 g, 57.1 mmol) and Compound amine47 (25.7 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 24.4 g of Compound 47. (Yield: 70%, MS: $[M+H]^+=612$)

Preparation Example 48

E amine48

48

Compound E (15 g, 57.1 mmol) and Compound amine48 (31 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 31.5 g of Compound 48. (Yield: 79%, MS: $[M+H]^+=700$)

465
Preparation Example 49

466
Preparation Example 50

E

+ amine49

Pd(t-Bu₃P)₂, K₂CO₃

THF/H₂O

49

F

+ amine50

Pd(t-Bu₃P)₂, K₂CO₃

THF/H₂O

50

Compound E (15 g, 57.1 mmol) and Compound amine49 (32.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 25.2 g of Compound 49. (Yield: 61%, MS: [M+H]⁺=724)

Compound F (15 g, 57.1 mmol) and Compound amine50 (26.5 g, 59.9 mmol) were added to 300 ml of THE under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 25.3 g of Compound 50. (Yield: 71%, MS: [M+H]⁺=624)

Preparation Example 51 amine51

51

Compound F (15 g, 57.1 mmol) and Compound amine51 (31 g, 59.9 mmol) were added to 300 ml of THF under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 12 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 25.2 g of Compound 51. (Yield: 63%, MS: $[M+H]^+=700$)

Preparation Example 52 amine52

52

Compound F (15 g, 57.1 mmol) and Compound amine52 (29.5 g, 59.9 mmol) were added to 300 ml of THF under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 28.1 g of Compound 52. (Yield: 73%, MS: $[M+H]^+=674$)

Preparation Example 53 amine53

Pd(t-Bu₃P)₂, K₂CO₃
THF/H₂O

-continued

53

Compound F (15 g, 57.1 mmol) and Compound amine53 (31 g, 59.9 mmol) were added to 300 ml of THF under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 12 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 25.9 g of Compound 53. (Yield: 65%, MS: [M+H]⁺=700)

Preparation Example 54 amine54

Pd(t-Bu₃P)₂, K₂CO₃
THF/H₂O

-continued

54

Compound F (15 g, 57.1 mmol) and Compound amine54 (34 g, 59.9 mmol) were added to 300 ml of THF under a nitrogen atmosphere, and the mixture was stirred and refluxed. Then, potassium carbonate (23.7 g, 171.3 mmol) was dissolved in 71 ml of water and added thereto, and the mixture was sufficiently stirred and then bis(tri-tert-butylphosphine)palladium(0) (0.3 g, 0.6 mmol) was added. After the reaction for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to prepare 30.4 g of Compound 54. (Yield: 71%, MS: $[M+H]^+=750$)

EXAMPLES

Example 1

A glass substrate on which a thin film of ITO (indium tin oxide) was coated in a thickness of 1,000 Å was put into distilled water containing the detergent dissolved therein and washed by the ultrasonic wave. In this case, the used detergent was a product commercially available from Fisher Co. and the distilled water was one which had been twice filtered by using a filter commercially available from Millipore Co. The ITO was washed for 30 minutes, and ultra-sonic washing was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, the following compound HI-1 was formed in a thickness of 1150 Å as a hole injection layer, but the following compound A-1 was p-doped at a concentration of 1.5 wt. %. The following compound HT-1 was vacuum deposited on the hole injection layer to form a hole transport layer with a film thickness of 800 Å. Then, Compound 1 prepared in Preparation Example 1 was vacuum-deposited on the hole transport layer to a thickness of 150 Å to form an electron blocking layer. Then, the following compound RH-1, and the following compound Dp-7 as a dopant were vacuum-deposited in a weight ratio of 98:2 on the electron blocking layer to form a red light emitting layer with a thickness of 400 Å. The following compound HB-1 was vacuum-deposited on the light emitting layer to a film thickness of 30 Å to form a hole blocking layer. Then, the following compound ET-1 and the following compound LiQ were vacuum-deposited in a weight ratio of 2:1 on the hole blocking layer to form an electron injection and transport layer with a thickness of 300 Å. Lithium fluoride (LiF) and aluminum were sequentially deposited to have a thickness of 12 Å and 1,000 Å, respectively, on the electron injection and transport layer, thereby forming a cathode.

473 474

HI-1

A-1

HT-1

RH-1

Dp-7

HB-1

-continued

ET-1

LiQ

In the above-mentioned processes, the deposition rates of the organic materials were maintained at 0.4~0.7 Å/sec, the deposition rates of lithium fluoride and the aluminum of the cathode were maintained at 0.3 Å/sec and 2 Å/sec, respectively, and the degree of vacuum during the deposition was maintained at $2\times10^{-7}$ to $5\times10^{-6}$ torr, thereby manufacturing an organic light emitting device.

Examples 2 to 54

The organic light emitting devices were manufactured in the same manner as in Example 1, except that the compounds shown in Table 1 below were used instead of Compound 1.

Comparative Examples 1 to 16

The organic light emitting devices were manufactured in the same manner as in Example 1, except that the compounds shown in Table 1 below were used instead of Compound 1. The structures of Compounds C-1 to C-16 in Table 1 are as follows.

C-1

C-2

C-3

477

-continued

C-4

C-5

C-6

C-7

478

-continued

C-8

C-9

C-10

479                                              480

-continued                                        -continued

C-11                                              C-15

C-12                                              C-16

C-13

C-14

Experimental Example

The driving voltage and efficiency were measured (15 mA/cm²) by applying a current to the organic light emitting devices manufactured in Examples 1 to 54 and Comparative Examples 1 to 16, and the results are shown in Table 1 below. Lifetime T95 means the time required for the luminance to be reduced to 95% of the initial luminance (6000 nit).

TABLE 1

| Category | Material | Driving voltage (V) | Efficiency (cd/A) | Lifetime T95 (hr) | Luminescent color |
|---|---|---|---|---|---|
| Example 1 | Compound 1 | 3.62 | 19.50 | 213 | Red |
| Example 2 | Compound 2 | 3.58 | 19.27 | 222 | Red |
| Example 3 | Compound 3 | 3.57 | 19.95 | 206 | Red |
| Example 4 | Compound 4 | 3.59 | 20.27 | 219 | Red |
| Example 5 | Compound 5 | 3.61 | 20.17 | 213 | Red |
| Example 6 | Compound 6 | 3.57 | 20.25 | 208 | Red |
| Example 7 | Compound 7 | 3.61 | 18.96 | 222 | Red |
| Example 8 | Compound 8 | 3.58 | 19.76 | 217 | Red |
| Example 9 | Compound 9 | 3.62 | 19.76 | 222 | Red |
| Example 10 | Compound 10 | 3.61 | 19.56 | 208 | Red |

TABLE 1-continued

| Category | Material | Driving voltage (V) | Efficiency (cd/A) | Lifetime T95 (hr) | Luminescent color |
|---|---|---|---|---|---|
| Example 11 | Compound 11 | 3.57 | 20.57 | 205 | Red |
| Example 12 | Compound 12 | 3.53 | 19.12 | 210 | Red |
| Example 13 | Compound 13 | 3.53 | 20.34 | 207 | Red |
| Example 14 | Compound 14 | 3.68 | 18.31 | 177 | Red |
| Example 15 | Compound 15 | 3.73 | 18.25 | 172 | Red |
| Example 16 | Compound 16 | 3.71 | 18.17 | 179 | Red |
| Example 17 | Compound 17 | 3.76 | 18.22 | 185 | Red |
| Example 18 | Compound 18 | 3.79 | 18.28 | 184 | Red |
| Example 19 | Compound 19 | 3.77 | 17.67 | 178 | Red |
| Example 20 | Compound 20 | 3.74 | 18.33 | 180 | Red |
| Example 21 | Compound 21 | 3.68 | 18.07 | 175 | Red |
| Example 22 | Compound 22 | 3.79 | 17.37 | 169 | Red |
| Example 23 | Compound 23 | 3.86 | 17.22 | 163 | Red |
| Example 24 | Compound 24 | 3.85 | 17.58 | 169 | Red |
| Example 25 | Compound 25 | 3.86 | 16.96 | 165 | Red |
| Example 26 | Compound 26 | 3.83 | 17.62 | 159 | Red |
| Example 27 | Compound 27 | 3.59 | 19.03 | 226 | Red |
| Example 28 | Compound 28 | 3.55 | 19.07 | 225 | Red |
| Example 29 | Compound 29 | 3.59 | 20.38 | 210 | Red |
| Example 30 | Compound 30 | 3.57 | 19.94 | 225 | Red |
| Example 31 | Compound 31 | 3.61 | 20.74 | 226 | Red |
| Example 32 | Compound 32 | 3.59 | 20.33 | 208 | Red |
| Example 33 | Compound 33 | 3.53 | 19.72 | 213 | Red |
| Example 34 | Compound 34 | 3.55 | 19.29 | 217 | Red |
| Example 35 | Compound 35 | 3.59 | 20.11 | 210 | Red |
| Example 36 | Compound 36 | 3.61 | 19.99 | 223 | Red |
| Example 37 | Compound 37 | 3.61 | 20.62 | 220 | Red |
| Example 38 | Compound 38 | 3.56 | 18.97 | 220 | Red |
| Example 39 | Compound 39 | 3.55 | 20.84 | 223 | Red |
| Example 40 | Compound 40 | 3.58 | 20.88 | 222 | Red |
| Example 41 | Compound 41 | 3.70 | 19.06 | 226 | Red |
| Example 42 | Compound 42 | 3.61 | 19.39 | 211 | Red |
| Example 43 | Compound 43 | 3.70 | 19.04 | 208 | Red |
| Example 44 | Compound 44 | 3.68 | 19.37 | 213 | Red |
| Example 45 | Compound 45 | 3.69 | 20.68 | 212 | Red |
| Example 46 | Compound 46 | 3.65 | 19.30 | 206 | Red |
| Example 47 | Compound 47 | 3.61 | 20.00 | 206 | Red |
| Example 48 | Compound 48 | 3.69 | 21.06 | 208 | Red |
| Example 49 | Compound 49 | 3.76 | 18.24 | 187 | Red |
| Example 50 | Compound 50 | 3.73 | 17.56 | 174 | Red |
| Example 51 | Compound 51 | 3.78 | 18.26 | 172 | Red |
| Example 52 | Compound 52 | 3.68 | 18.25 | 170 | Red |
| Example 53 | Compound 53 | 3.76 | 17.51 | 170 | Red |
| Example 54 | Compound 54 | 3.79 | 18.17 | 177 | Red |
| Comparative Example 1 | Compound C-1 | 4.11 | 14.97 | 125 | Red |
| Comparative Example 2 | Compound C-2 | 4.06 | 14.88 | 112 | Red |
| Comparative Example 3 | Compound C-3 | 4.28 | 13.48 | 91 | Red |
| Comparative Example 4 | Compound C-4 | 4.26 | 14.58 | 96 | Red |
| Comparative Example 5 | Compound C-5 | 4.23 | 14.30 | 92 | Red |
| Comparative Example 6 | Compound C-6 | 4.19 | 14.60 | 93 | Red |
| Comparative Example 7 | Compound C-7 | 4.46 | 13.41 | 81 | Red |
| Comparative Example 8 | Compound C-8 | 4.39 | 12.48 | 63 | Red |
| Comparative Example 9 | Compound C-9 | 4.15 | 14.88 | 121 | Red |
| Comparative Example 10 | Compound C-10 | 4.42 | 12.18 | 64 | Red |
| Comparative Example 11 | Compound C-11 | 4.41 | 12.32 | 57 | Red |
| Comparative Example 12 | Compound C-12 | 4.22 | 15.28 | 103 | Red |
| Comparative Example 13 | Compound C-13 | 4.18 | 15.11 | 101 | Red |
| Comparative Example 14 | Compound C-14 | 4.09 | 15.36 | 126 | Red |

TABLE 1-continued

| Category | Material | Driving voltage (V) | Efficiency (cd/A) | Lifetime T95 (hr) | Luminescent color |
|---|---|---|---|---|---|
| Comparative Example 15 | Compound C-15 | 4.17 | 15.06 | 94 | Red |
| Comparative Example 16 | Compound C-16 | 4.38 | 13.33 | 77 | Red |

When a current was applied to the organic light emitting devices manufactured in Examples 1 to 54 and Comparative Examples 1 to 16, the results shown in Table 1 were obtained. In the Examples and Comparative Examples, a material widely used in the prior art was used as a material excluding the electron blocking layer, and Dp-7 was used as a dopant of the red light emitting layer.

According to the results in Table 1 above, when the compound of the present disclosure was used as the electron blocking layer, the driving voltage was significantly lowered and the efficiency was also increased, as compared with Comparative Examples. In this respect, it was found that the energy transfer from the host to the red dopant was successful. In addition, it was also found that the lifetime characteristics could be greatly improved while maintaining high efficiency.

In conclusion, when the compound of the present disclosure was used as the electron blocking layer of the red light emitting layer, it was confirmed that the driving voltage, luminous efficiency and lifetime characteristics of the organic light emitting device could be improved.

DESCRIPTION OF REFERENCE NUMERALS

1: substrate
2: anode
3: electron blocking layer
4: light emitting layer
5: cathode
6: hole injection layer
7: hole transport layer
8: hole blocking layer
9: electron transport and injection layer

The invention claimed is:

1. A compound represented by the following Chemical Formula 1:

[Chemical Formula 1]

in Chemical Formula 1, one of $R_1$ to $R_{12}$ is a substituent represented by the following Chemical Formula 2, and the rest of $R_1$ to $R_{12}$ are each independently hydrogen or deuterium,

483

484

-continued

[Chemical Formula 2]

10 in Chemical Formula 2, $L_1$ is a substituted or unsubstituted phenylene, a substituted or unsubstituted biphenyldiyl, a substituted or unsubstituted naphthalenediyl, or

$L_2$ and $L_3$ are each independently a single bond; a substituted or unsubstituted $C_{6-60}$ arylene; or a substituted or unsubstituted $C_{2-60}$ heteroarylene containing one or more selected from the group consisting of N, O and S,

Ar$_1$ is a substituted or unsubstituted $C_{6-60}$ aryl; or a substituted or unsubstituted $C_{2-60}$ heteroaryl containing one or more selected from the group consisting of N, O and S, and

Ar$_2$ is biphenylyl, terphenylyl, naphthyl, phenanthrenyl, phenyl naphthyl, dibenzofuranyl, dibenzothiophenyl, phenyl carbazolyl, dimethyl fluorenyl, benzonaphthofuranyl, or benzonaphthothiophenyl.

2. The compound of claim 1, wherein $L_1$ is one selected from the following:

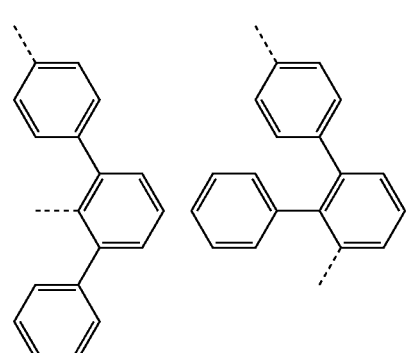

485

486

-continued

4. The compound of claim 1, wherein $L_2$ and $L_3$ are each independently a single bond or one selected from the following:

3. The compound of claim 1, wherein $L_2$ and $L_3$ are each independently a single bond, phenylene, phenylene substituted with one phenyl, biphenyldiyl, biphenyldiyl substituted with one phenyl, or naphthalenediyl.

5. The compound of claim 1, wherein $Ar_1$ is phenyl, biphenylyl, terphenylyl, naphthyl, phenanthrenyl, phenyl naphthyl, dibenzofuranyl, dibenzothiophenyl, phenyl carbazolyl, dimethyl fluorenyl, benzonaphthofuranyl, or benzonaphthothiophenyl.

6. The compound of claim 1, wherein Ar$_1$ is one selected from the following:

488

489
-continued

490
-continued

7. The compound of claim 1, wherein Ar$_2$ is one selected from the following:

491

492

-continued

-continued

493

494

8. The compound of claim 1, wherein the compound represented by Chemical Formula 1 is one
    selected from the following:

495

496

497

498

499

500

501

-continued

502

-continued

503

504

505

506

507

508

509

510

511

512

513
-continued

514
-continued

515

516

517

-continued

518

-continued

519

520

521

-continued

522

-continued

523

524

525

526

527

528

529

530

531

-continued

532

-continued

533
-continued

534
-continued

535

536

537
-continued

538
-continued

539

540

541

542

543

544

545

546

547

548

549

550

551

552

553

554

555

-continued

556

-continued

557

-continued

558

-continued

559

-continued

560

-continued

561

562

563

564

565
-continued

566

567
-continued

568
-continued

569

570

571
-continued

572
-continued

573
-continued

574
-continued

575

576

577

578

579

580

581

-continued

582

-continued

583

584

585

-continued

586

-continued

587

588

589

590

591

592

593

594

595
-continued

596
-continued

597
-continued

598
-continued

599

600

601

-continued

602

-continued

603
-continued

604
-continued

605

606

607

-continued

608

-continued

609

610

611

612

613

614

615

616

617
-continued

618
-continued

619

-continued

620

-continued

621
-continued

622
-continued

623

-continued

624

-continued

625

-continued

626

-continued

627

-continued

628

-continued

629

630

631

632

633

634

635

636

637
-continued

638
-continued

639

640

641

642

643
-continued

644
-continued

645

-continued

646

-continued

647

648

649

650

651

652

653

654

655

656

657

658

659

660

661

662

663

664

665

-continued

666

-continued

667

668

669

670

671

672

673

674

675
-continued

676
-continued

677
-continued

678
-continued

679

680

681
-continued

682
-continued

683
-continued

684
-continued

685

686

687

688

689

690

691

692

693
-continued

694
-continued

695

696

697

698

699

700

701

702

703

704

705

706

707

708

709

-continued

710

-continued

711

-continued

712

-continued

713

-continued

714

-continued

715

-continued

716

-continued

717
-continued

718
-continued

719

720

721

722

723

724

725
-continued

726
-continued

727

728

729

730

731

732

-continued

-continued

733
-continued

734
-continued

735

736

737

738

739

740

741

742

743
-continued

744
-continued

745

746

747

748

749

750

751

752

753

-continued

754

-continued

755

756

757
-continued

758
-continued

759

760

761

-continued

762

-continued

763

764

765

766

767

768

769

770

771
-continued

772
-continued

773

774

775

776

777

778

779
-continued

780
-continued

781

782

783

784

785
-continued

786
-continued

787

-continued

788

-continued

789

790

791

-continued

792

-continued

793

794

795

796

797

798

799

800

801

802

803
-continued

804
-continued

805

806

807

808

809
-continued

810
-continued

811

812

813
-continued

814
-continued

815

816

817

818

819

820

821

822

823
-continued

824
-continued

825

826

827
-continued

828
-continued

829
-continued

830
-continued

831

832

833
-continued

834
-continued

835

836

837

838

839

840

841

842

843

844

845
-continued

846
-continued

847

-continued

848

9. An organic light emitting device comprising:

a first electrode;

a second electrode disposed to face the first electrode; and an organic material layer including one or more layers between the first electrode and the second electrode, wherein one or more layers of the organic material layer comprise the compound as set forth in claim 1.

10. The organic light emitting device of claim 9, wherein the organic material layer includes a light emitting layer, and wherein the light emitting layer comprises the compound.

11. The organic light emitting device of claim 9, wherein the organic material layer includes an electron blocking layer, and wherein the electron blocking layer comprises the compound.

* * * * *